US00PP24852P3

(12) United States Plant Patent
Leelachaikul

(10) Patent No.: US PP24,852 P3
(45) Date of Patent: Sep. 9, 2014

(54) *ADENIUM* PLANT NAMED 'LEELADE202'

(50) Latin Name: *Adenium obesum*
Varietal Denomination: LEELADE202

(76) Inventor: Anong Leelachaikul, Bangkok (TH)

( * ) Notice: Subject to any disclaimer, the term of this patent is extended or adjusted under 35 U.S.C. 154(b) by 30 days.

(21) Appl. No.: 13/573,429

(22) Filed: Sep. 15, 2012

(65) Prior Publication Data

US 2014/0082792 P1 Mar. 20, 2014

(51) Int. Cl.
*A01H 5/00* (2006.01)

(52) U.S. Cl.
USPC ..... Plt./226

(58) Field of Classification Search
USPC ..... Plt./263.1, 226, 373
See application file for complete search history.

*Primary Examiner* — Kent L Bell
(74) *Attorney, Agent, or Firm* — Cassandra Bright

(57) ABSTRACT

A new and distinct *Adenium* cultivar named 'LEELADE202' is disclosed, characterized by unique double white and red-purple flowers. The new variety is a *Adenium*, typically produced as an indoor ornamental plant.

1 Drawing Sheet

Latin name of the genus and species: *Adenium obesum.*
Variety denomination: 'LEELADE202'.

BACKGROUND OF THE INVENTION

This application relates to a new cultivar of *Adenium obesum*. The new variety is the product of a planned breeding program. The new variety originated as a seedling from the crossing of the unpatented, proprietary seed parent *Adenium obesum* 'VCKRWI' with the unpatented, proprietary pollen parent referred to as *Adenium obesum* 'VKGW4'. The crossing was made by the inventor in a non-commercial nursery in Bangkok, Thailand during 2006.

The new variety was first selected by the inventor, Anong Leelachaikul, a citizen of Thailand, in June 2009, at the same nursery in Bangkok, Thailand. After identifying the new variety as a potentially interesting selection, the inventor continued confidential testing and propagation of 'LEELADE202', assessing stability of the unique characteristics of this variety.

Asexual reproduction of the new cultivar 'LEELADE202' was first performed in June 2009 at a commercial nursery in Bangkok, Thailand by taking a nodal cutting from the new variety and grafting that to a rootstock plant. The rootstock plants are started from seed, and are unnamed, unpatented varieties of *Adenium obesum*. Access to all plants was restricted, as plants were kept in a greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'LEELADE202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LEELADE202'. These characteristics in combination distinguish 'LEELADE202' as a new and distinct *Adenium* cultivar:

1. Flower configuration with a consistent full second row of petals, forming a double flower.
2. Unique mixed flower color of white and red-purple.

PARENT COMPARISON

Plants of the new cultivar 'LEELADE202' are similar to the seed parent, *Adenium* 'VCKRWI' in most horticultural characteristics. The new variety, however, produces double flowers whereas the seed parent produces single flowers.

Plants of the new cultivar 'LEELADE202' are similar to the pollen parent, *Adenium* 'VKGW4' in most horticultural characteristics. The new variety, however, produces flowers with two colors, whereas the pollen parent produces a single color flower.

COMMERCIAL COMPARISON

Plants of the new cultivar 'LEELADE202' are similar to the commercial variety *Adenium* 'Double Moons' in most horticultural characteristics. However, the new variety differs in the following characteristics:

1. Different leaf shape
2. Different petal shape
3. 'Double Moons' has a flower with more pink coloration than 'LEELADE202'

Plants of the new cultivar 'LEELADE202' are similar to the commercial variety, *Adenium* 'Sweet Blossom' in most horticultural characteristics. However, the new variety differs in the following characteristics:

1. Different petal shape
2. Different margin characteristics, 'Sweet Blossom' does not have a wavy margin.
3. 'Sweet Blossom' has flowers with different color patterns than 'LEELADE202'

BRIEF DESCRIPTION OF THE PHOTOGRAPH

The accompanying photograph in FIG. 1 illustrates in full color a typical plant of 'LEELADE202' grafted outdoors in Thailand and grown in a commercial greenhouse in Honselersdijk, the Netherlands. This plant is approximately 9 months old from the graft, shown planted in 15 cm container. The plant has been grown according to the details in the following paragraph. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'LEELADE202' plants grown according to the following protocols.

Taking place in a commercial nursery, outdoors in Bangkok, Thailand, rootstock is grown from seeds. Seeds are planted and grown for 12-14 months. After that, heads are taken off the rootstock plants and the plants are grafted together with the selected variety.

Grafting is done by means of taking a nodal cutting from the candidate variety and placing that on top of the cut of the rootstock plant. Immediately after that, the top of the plant is covered by a layer of plastic and tied down by a rubber band. The plastic covers the actual graft entirely.

Rootstock plants during the first few weeks after seeding are grown under shade, and after that they are grown in Thailand in full sun. Stock plants of the candidate variety, resulting in the nodal cutting are also grown in Thailand in full sun.

During and until 1-2 weeks after grafting, plants are placed in a greenhouse that has both shade cloth and overhead plastic. This protects the grafted plants against the sun and the rain. After that, the grafted plants are placed in full sun again.

Three to four months after grafting, the grafted plants are cut back and shipped to the Netherlands. In the Netherlands, the plants continue to grow for 3-5 months, after which they are sold as flowering plant. Therefore, counted from the date of grafting, it takes 6-9 months to produce a finished flowering plant.

In Thailand the plants grow under natural outdoor conditions, with temperatures ranging from approximately 10° C. to 40° C., and very bright sunlight. In the Netherlands, the plants are grown in a greenhouse with average day temperature about 26 degrees Celsius and average night temperature about 22 degrees Celsius, un-shaded, to allow as much natural light as possible.

Measurements and numerical values below represent averages of typical plant types.

Botanical classification: *Adenium obesum* 'LEELADE202'.

PROPAGATION

Root description: The plant described is grafted and does not have its own roots for description.

PLANT

Caudex description:

- *Diameter*.—Average: 4.6 cm.
- *Height*.—Average: 7.5 cm.
- *Color*.—Greyed-green, near RHS 194A but slightly darker.
- *Texture*.—Smooth, very slightly glossy.

Plant spread: Approximately 19.4 cm.

Plant height: Top of flowering plane, average: 28.5 cm. Top of foliar plane, average: 28.5 cm.

Growth rate: Moderate.

Length of primary stem: Approximately 6.2 cm.

Diameter of primary stem: Approximately 1.9 cm.

Stem color: Greyed-green, a color in between RHS 191A, 198B and 198C.

Stem texture: Smooth, very slightly glossy.

Lateral branches:

- *Quantity*.—3 (after pinching).
- *Length*.—8.7 cm.
- *Diameter*.—0.8 cm.
- *Color*.—Young stems yellow-green, near RHS 144C, older stems greyed-green near RHS 191B.
- *Texture/pubescence*.—Smooth, moderately glossy.

Internode length: Approximately 0.6 cm.

Age of plant described: Approximately 6 to 9 months from grafting onto a 12 month old rootstock. Grafted plants grown in the Netherlands, in a commercial greenhouse.

FOLIAGE

Leaf:

- *Arrangement*.—Alternate.
- *Quantity*.—Approximately 21 per lateral branch.
- *Average length*.—Approximately 6.8 cm.
- *Average width*.—Approximately 3.8 cm.
- *Shape of blade*.—Oblanceolate.
- *Apex*.—Abruptly acute.
- *Base*.—Narrow cuneate.
- *Attachment*.—Sessile.
- *Margin*.—Entire.
- *Texture of top surface*.—Smooth, glossy.
- *Texture of bottom surface*.—Smooth, matte.
- *Pubescence*.—No pubescence.
- *Color*.—Young foliage upper side: Green; near RHS 143C. Young foliage under side: Yellow-green; near RHS 147D. Mature foliage upper side: Green; near RHS N137B. Mature foliage under side: Green; near RHS 138B.
- *Venation*.—Type: Pinnate. Venation color upper side: Greyed-green; near RHS 192B. Venation color under side: Greyed-green; near RHS 193A.

Petiole: No petioles present, leaves sessile.

FLOWERING CHARACTERISTICS

Natural flowering season: In Thailand, the plants flower all year around, but during heavy rain periods, the plants do drop most or all of their flowers. Therefore, especially during the rainy seasons in Thailand, the plants will not flower so heavily as during the dry seasons. In The Netherlands, the plants will naturally flower most heavily during periods of very heavy sun and long days, particularly in July and August and to a lesser extent in June and September.

Inflorescence type and habit: Axillary compound cyme.

Flower longevity on plant: Average: After the opening of the flowers, the flowers will stay on the plant on average between 5-10 days. How long the flowers stay on the plants mostly depend on climate conditions like the light level, day length, amount of watering.

Quantity of flowers: About 29 buds and 2 fully opened flowers per plant, at one time.

Inflorescence size:
*Diameter*.—Approximately 10.4 cm.
*Height*.—Approximately 6.6 cm.
Individual flower size:
*Diameter*.—Average: 6.6 cm.
*Flower tube length*.—Average: 4.0 cm.
*Flower tube diameter at distal end*.—Average: 1.9 cm.
*Flower tube diameter at proximal end*.—Average: 0.4 cm.
Petals:
*Petal arrangement*.—Rotate.
*Length from throat*.—Average: 3.1 cm.
*Width*.—Average: 3.0 cm.
*Quantity*.—Average: 5.
*Texture*.—Smooth, slightly velvety, dull.
*Margin*.—Entire, wavy.
*Tip shape*.—Rounded to retuse.
*Petaloids*.—Average: 10, average length from throat: 2.7 cm, average width: 2.5 cm, texture: smooth, slightly velvety, dull, margins entire, wavy, tip shaped broad acute.
Color:
*Petals*.—When opening: Upper surface: Red-purple; near RHS 69B, 69C and 69D, with an irregular narrow central blotch colored red-purple; RHS N57A, outer margins red-purple; RHS 61B and 70B. Lower surface: Red-purple; near RHS 58C and 58D, base purple; RHS 76D, outer margins red-purple; RHS 61B. Fully opened: Upper surface: Red-purple; near RHS 69B, with an irregular narrow central blotch colored red-purple; RHS N57A, outer margins red-purple; RHS 61B and 70B. Lower surface: Red-purple; near RHS 58C, base purple; RHS 76D, outer margins red-purple; RHS 61B. Flower throat (inside): White; 155A. Flower throat, vein: White; 155A. Flower tube (outside): Green-yellow; near RHS 1D. Flower tube, vein: Green-yellow; near RHS 1D. Fading: Petals fading to: Not fading.
Color:
*Petaloids*.—When opening: Upper surface: Red-purple; near RHS 69B, with an irregular narrow central blotch colored red-purple; RHS N57A, outer margins red-purple; RHS 71C. Lower surface: Red-purple; near RHS 58C and 58D, base red-purple; RHS 69D, outer margins red-purple; RHS 61B. Fully opened: Upper surface: Red-purple; near RHS 69B, 69C and 69D, with an irregular narrow central blotch colored red-purple; RHS N57A, outer margins red-purple; RHS 61B and 70B. Lower surface: Red-purple; near RHS 63C, base purple; RHS 76D, outer margins red-purple; RHS 61B. Fading: Petaloids fading to: Not fading.
Bud:
*Shape*.—Oblanceolate.
*Length*.—Average: 2.8 cm.
*Diameter*.—Average: 0.7 cm.
*Color*.—Yellow-green; near RHS 145C, top red; RHS 54A and 54B.
Peduncle:
*Length*.—Average: 0.4 cm.
*Diameter*.—Average; 0.4 cm.
*Color*.—Yellow-green; near RHS 145A and 145B.
*Orientation*.—Outward.
*Strength*.—Moderately strong.
Pedicel:
*Length*.—Average: 0.8 cm.
*Diameter*.—Average: 0.3 cm.
*Color*.—Yellow-green; near RHS 145B.
*Orientation*.—Outward to upright.
*Strength*.—Moderately strong.
Sepals:
*Quantity per flower*.—Average: 5.
*Shape*.—Narrow ovate.
*Length*.—Approximately 0.9 cm.
*Width*.—Approximately 0.3 cm.
*Margin*.—Entire.
*Texture*.—Smooth.
*Color*.—Upper and lower surfaces Yellow-green; near RHS 145B.
*Apex*.—Mucronulate.

REPRODUCTIVE ORGANS

Stamens:
*Number*.—Average: 5.
*Filament length*.—Approximately 0.4 cm.
Anthers:
*Shape*.—Linear.
*Length*.—Approximately 2.8 cm.
*Color*.—Ranging Red-purple to white; near RHS 62D and N155B.
*Pollen*.—Color: No pollen detected.
Pistil:
*Number*.—Average: 1.
*Length*.—Approximately 1.5 cm.
*Style*.—Length: Approximately 1.45 cm. Color: Yellow-green; near RHS 145D.
*Stigma*.—Shape: Club-shaped. Color: Yellow-green; near RHS 145B. Ovary color: Yellow-green; near RHS 145C.

OTHER CHARACTERISTICS

Disease resistance: Good resistance to the normal diseases found in *Adenium*.
Drought tolerance and cold tolerance: Normal for species, USDA zone 10 and higher.
Fruit/seed production: No fruits/seeds detected to date.

What is claimed is:

1. A new and distinct cultivar of *Adenium* plant named 'LEELADE202' as herein illustrated and described.

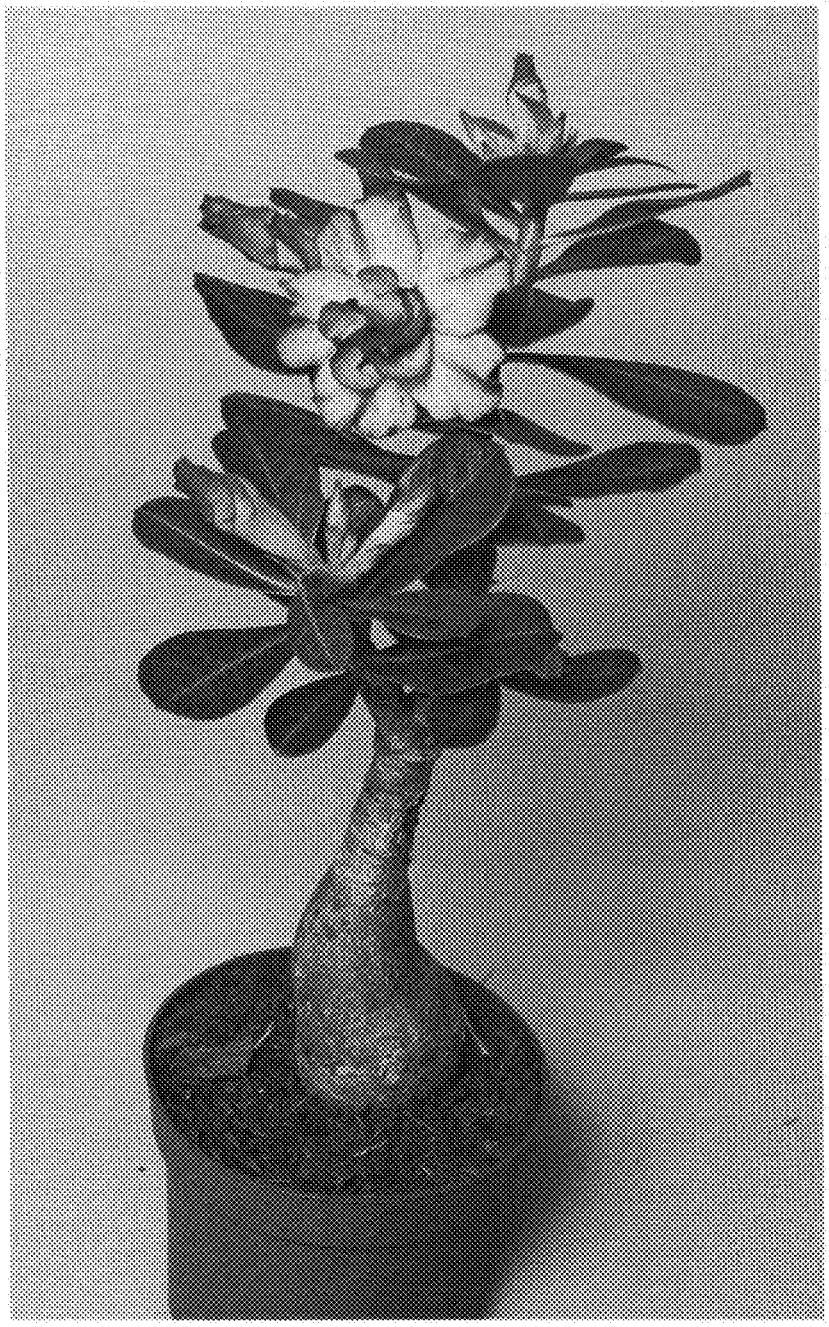

* * * * *